(12) United States Patent
Carter et al.

(10) Patent No.: US 9,057,723 B2
(45) Date of Patent: Jun. 16, 2015

(54) METHOD FOR SENSING A CHEMICAL

(75) Inventors: Timothy Joseph Nicholas Carter, Sittingbourne (GB); Steven Andrew Ross, Sittingbourne (GB)

(73) Assignee: Vivacta Ltd., Sittingbourne, Kent (GB)

( * ) Notice: Subject to any disclaimer, the term of this patent is extended or adjusted under 35 U.S.C. 154(b) by 999 days.

(21) Appl. No.: 12/935,322

(22) PCT Filed: Mar. 31, 2009

(86) PCT No.: PCT/GB2009/050310
§ 371 (c)(1),
(2), (4) Date: Dec. 22, 2010

(87) PCT Pub. No.: WO2009/122206
PCT Pub. Date: Oct. 8, 2009

(65) Prior Publication Data
US 2011/0086365 A1 Apr. 14, 2011

Related U.S. Application Data

(60) Provisional application No. 61/041,823, filed on Apr. 2, 2008.

(30) Foreign Application Priority Data

Apr. 2, 2008 (GB) .................................... 0805950.3
Sep. 16, 2008 (GB) .................................... 0816924.5

(51) Int. Cl.
*G01N 33/551* (2006.01)
*G01N 33/543* (2006.01)
*G01N 21/17* (2006.01)
*G01N 33/542* (2006.01)

(52) U.S. Cl.
CPC ........ *G01N 33/5438* (2013.01); *G01N 21/1702* (2013.01); *G01N 21/171* (2013.01); *G01N 33/542* (2013.01); *G01N 2021/1708* (2013.01)

(58) Field of Classification Search
None
See application file for complete search history.

(56) References Cited

U.S. PATENT DOCUMENTS 4,444,879 A * 4/1984 Foster et al. .................. 435/7.95
5,622,868 A * 4/1997 Clarke et al. .................. 436/147

FOREIGN PATENT DOCUMENTS

WO 2004090512 A 10/2004

OTHER PUBLICATIONS

Maggio et al, "Enzyme Immunoassay", CRC Press, 1980, p. 61.*

*Primary Examiner* — Chris L Chin
(74) *Attorney, Agent, or Firm* — Rothwell, Figg, Ernst & Manbeck, P.C.

(57) ABSTRACT

The present invention relates to a method for detecting an analyte (10) in a sample, comprising the steps of: providing a transducer (3) having a pyroelectric or piezoelectric element and electrodes which is capable of transducing a change in energy to an electrical signal, a first reagent (9) immobilized on the transducer, the first reagent having a binding site which is capable of binding the analyte or a derivative of the analyte, exposing the sample to the transducer thereby allowing the analyte or a derivative of the analyte to bind to the first reagent to form a first reagent-analyte complex (13); introducing a second reagent (11), the second reagent having a binding site which is capable of selectively binding the first reagent-analyte complex, wherein the second reagent has a label (12) attached thereto which is capable of absorbing electromagnetic radiation to generate energy by non-radiative decay; irradiating the sample with electromagnetic radiation; transducing the energy generated into an electrical signal; and detecting the electrical signal. The invention also provides a kit for carrying out the method.

19 Claims, 4 Drawing Sheets

METHOD FOR SENSING A CHEMICAL

This application is a filing under 35 USC 371 of PCT/GB2009/050310, filed Mar. 31, 2009, which claims priority from GB 0805950.3, filed Apr. 2, 2008, U.S. 61/041,823, filed Apr. 2, 2008 and GB 0816924.5, filed Sep. 16, 2008. These prior applications are incorporated herein by reference.

The present invention relates to a method for sensing a chemical, and in particular to an immunoassay employing a chemical sensing device containing a piezo/pyroelectric transducer.

An immunoassay is a test which measures the presence or more usually the concentration of an analyte in a biological fluid. It typically involves the specific binding of an antigen to an antibody. The antibody can be polyclonal or monoclonal, monoclonal antibodies having several benefits, including reproducibility of manufacture and containment of binding to one epitope of an analyte. In order to provide a quantifiable measure of the concentration of the analyte, the response is compared to standard samples of known concentration. The concentration of the antibody or antigen may be determined by a variety of methods, although one of the most common is to label either the antigen or antibody and detect the presence of the label.

Immunoassays can be competitive or non-competitive. In a competitive immunoassay, the antigen in the unknown sample competes with labelled antigen to bind to antibodies, which are typically immobilised on a solid phase. The amount of labelled antigen bound to the antibody site is then measured, usually by separating and measuring the labelled antigen bound to the solid phase. Clearly the response will be inversely proportional to the concentration of antigen in the unknown sample. In an analogous assay principle, labelled antibody in solution competes with antigen immobilised on a solid phase and that present in the sample, giving a similar inverse proportionality. In a non-competitive immunoassay, also referred to as an immunometric assay, the antigen in the unknown sample binds to an excess of immobilised antibodies (the "capture" antibodies) and the amount of bound antigen is measured. Unlike the competitive method, the results of the non-competitive method will be directly proportional to the concentration of the antigen. In a so-called "two-site" immunometric assay, also termed a "sandwich assay", the antigen is bound to the capture antibody site, and then labelled antibody is introduced which binds to the antigen bound to the capture antibody. The amount of labelled antibody at the site is then measured.

In a typical sandwich immunoassay, an antibody specific for an antigen of interest is attached to a polymeric support such as a sheet of polystyrene. A drop of the sample to be tested, e.g. a cell extract or a sample of serum or urine, is laid on the sheet, which is washed after formation of the antibody-antigen complex. Antibody specific for a different site on the antigen is then added, and the support is again washed. This second antibody carries a label (the labelled reporter) so that it can be detected with high sensitivity. The amount of second antibody bound to the sheet is proportional to the quantity of antigen in the sample. This assay and other variations on this type of assay are well known, see, for example, "The Immunoassay Handbook, 2nd Ed." David Wild, Ed., Nature Publishing Group, 2001.

Immunoassays of this type work particularly well for large molecular mass analytes, principally because two or more epitopes may be addressed; areas of complementarity between analyte and antibody are relatively large and relatively large differences occur between analytes, e.g. by at least an amino acid in peptides. With small molecule immunoassays, the absence of two epitopes prohibits the formation of a "sandwich". This has provided motivation for further techniques to be developed.

One relatively new immunoassay technique is the so-called "anti-complex antibody" immunoassay which is designed to improve specificity and sensitivity of small molecule detection (see C. H. Self at al. Clin. Chem. 1994, 40, 2035-2041; ibid 1994, 40, 2035-2041; and L. A. Winger et al J. Immunol. Methods 1996, 199, 185-191). This immunoassay also has the advantage that it provides a direct relationship between the concentration of the analyte and signal, rather than the inverse relationship commonly seen in competitive immunoassays.

The protocol is based on the ability to raise secondary antibodies to the complex formed when the small molecule analyte binds to a specifically raised primary antibody which is immobilised on (attached to) a support. By judicious selection of the second antibody, reactivity can be chosen against an epitope formed at the junction of the primary antibody and the antigen. The binding to the complex is therefore selective in that the labelled reporter cannot bind to the "unoccupied" capture antibody or to the free analyte since the epitope is not generated until the first binding event occurs. This has been shown to be very sensitive and specific but, as currently practiced, requires a number of washing steps, most importantly to eliminate excess unbound label before determination of the amount of labelled antibody present. This significantly adds to the complexity of the assay and substantially limits the applicability of the technique.

Accordingly, the present invention provides a method for detecting an analyte in a sample, comprising the steps of:
providing a transducer having a pyroelectric or piezoelectric element and electrodes which is capable of transducing a change in energy to an electrical signal, a first reagent immobilised on the transducer, the first reagent having a binding site which is capable of binding the analyte or a derivative of the analyte,
exposing the sample to the transducer thereby allowing the analyte or a derivative of the analyte to bind to the first reagent to form a first reagent-analyte complex;
introducing a second reagent, the second reagent having a binding site which is capable of selectively binding the first reagent-analyte complex, wherein the second reagent has a label attached thereto which is capable of absorbing electromagnetic radiation to generate energy by non-radiative decay;
irradiating the sample with electromagnetic radiation;
transducing the energy generated into an electrical signal; and
detecting the electrical signal.

Thus, the labelled second reagent (the reporter) can only bind to the complex of the first reagent (immobilised capture reagent) and analyte. No binding of the reporter to the transducer surface takes place in the absence of the analyte, rather like a conventional two-site immunometric immunoassay. However, in this case the reporter only requires a single epitope (generated from the analyte-first reagent complex) rather than the two required for a conventional sandwich assay, thereby facilitating small molecule detection. As a result of the use of a transducer having a piezo/pyroelectric film, the benefit of being able to detect the binding of the second (labelled) reagent in real time without separation and washing steps is achieved.

The present invention also provides a kit comprising: (i) a device for detecting an analyte in a sample comprising a transducer having a pyroelectric or piezoelectric element and electrodes which is capable of transducing a change in energy to an electrical signal, a first reagent immobilised on the transducer, the first reagent having a binding site which is capable of binding the analyte or a derivative of the analyte, a source of electromagnetic radiation, and a detector for detecting the electrical signal; and (ii) a second reagent, the second reagent having a binding site which is capable of selectively binding a complex formed between the first reagent and the analyte or the derivative of the analyte, wherein the second reagent has a label attached thereto which is capable of absorbing the electromagnetic radiation generated by the radiation source to generate energy by non-radiative decay. The present invention further provides the use of a transducer having a pyroelectric or piezoelectric element and electrodes for detecting a binding event in an anti-complex antibody immunoassay.

The present invention will now be described with reference to the drawings, in which.

Figure 1:
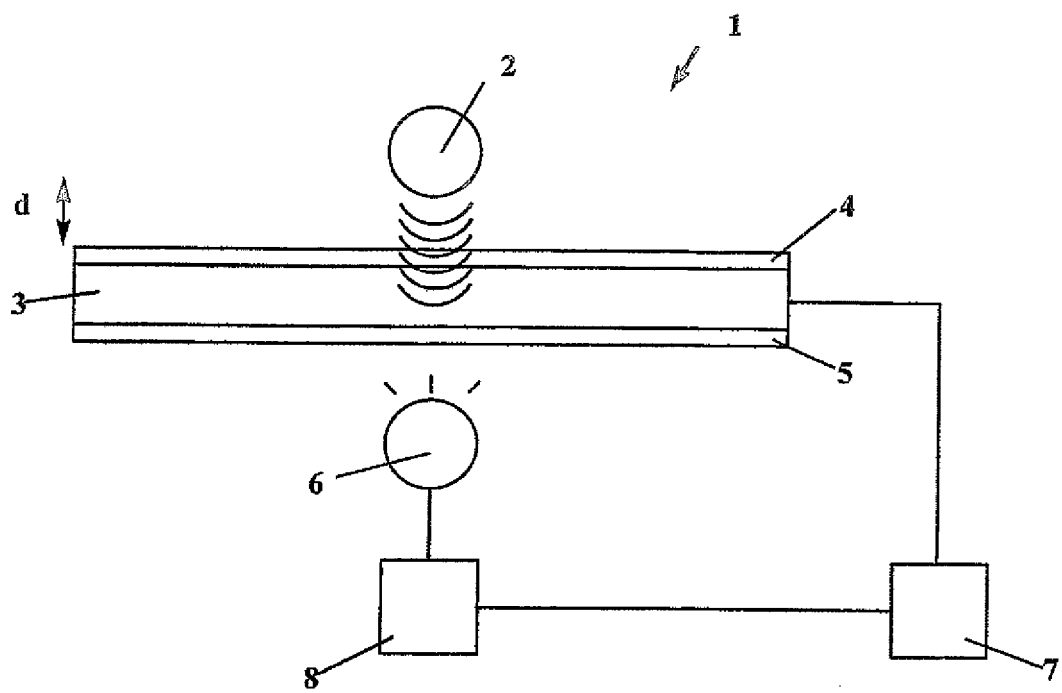
FIG. 1 shows a device according to WO 2004/090512.

The method of the present invention provides for the detection of an analyte in a sample. As a first step, the method includes the provision of a transducer having a pyroelectric or piezoelectric element and electrodes which is capable of transducing a change in energy to an electrical signal and exposing the sample to the transducer. Such transducers are known in the art, see for example WO 90/13017 and WO 2004/090512. In this regard, FIG. 1 shows the principle of the chemical sensing device 1 suitable for use in the present invention. The device 1 relies on heat generation in a substance 2 on irradiation of the substance 2 with electromagnetic radiation. The device 1 comprises a pyroelectric or piezoelectric transducer 3 having electrode coatings 4,5. The transducer 3 is preferably a film, e.g. a poled polyvinylidene fluoride film. The electrode coatings 4,5 are preferably formed from indium tin oxide having a thickness of about 35 nm, although almost any thickness is possible from a lower limit of 1 nm below which the electrical conductivity is too low and an upper limit of 100 nm above which the optical transmission is too low (it should not be less than 95% T). A substance 2 is held on or proximal to the transducer 3 using any suitable technique, shown here attached to the upper electrode coating 4. The reagent may be in any suitable form and a plurality of reagents may be deposited. Preferably, the substance 2 is adsorbed on to the upper electrode, e.g. covalently coupled or bound via intermolecular forces such as ionic bonds, hydrogen bonding or van der Waal's forces. A key feature of this device is that the substance 2 generates heat when irradiated by a source of electromagnetic radiation 6, such as light, preferably visible light. The light source may be, for example, an LED. The light source 6 illuminates the substance 2 with light of the appropriate wavelength (e.g. a complementary colour). Although not wishing to be bound by theory, it is believed that the substance 2 absorbs the light to generate an excited state which then undergoes non-radiative decay thereby generating energy, indicated by the curved lines in FIG. 1. This energy is primarily in the form of heat (i.e. thermal motion in the environment) although other forms of energy, e.g. a shock wave, may also be generated. The energy is, however, detected by the transducer and converted into an electrical signal. The device of the present invention is calibrated for the particular reagent being measured and hence the precise form of the energy generated by the non-radiative decay does not need to be determined. Unless otherwise specified the term "heat" is used herein to mean the energy generated by non-radiative decay. The light source 6 is positioned so as to illuminate the substance 2. Preferably, the light source 6 is positioned substantially perpendicular to the transducer 3 and electrodes 4,5 and the substance 2 is illuminated through the transducer 3 and electrodes 4,5. The light source may be an internal light source within the transducer in which the light source is a guided wave system. The wave guide may be the transducer itself or the wave guide may be an additional layer attached to the transducer. The wavelength of illumination depends on the label used; for example, for 40 nm gold labels the preferred wavelength is 525 nm and for carbon labels the preferred wavelength is 650 nm.

The energy generated by the substance 2 is detected by the transducer 3 and converted into an electrical signal. The electrical signal is detected by a detector 7. The light source 6 and the detector 7 are both under the control of the controller 8.

In one embodiment, the light source 6 generates a series of pulses of light (the term "light" used herein means any form of electromagnetic radiation unless a specific wavelength is mentioned) which is termed "chopped light". In principle, a single flash of light, i.e. one pulse of electromagnetic radiation, would suffice to generate a signal from the transducer 3. However, in order to obtain a reproducible signal, a plurality of flashes of light are used which in practice requires chopped light. The frequency at which the pulses of electromagnetic radiation are applied may be varied. At the lower limit, the time delay between the pulses must be sufficient for the time delay between each pulse and the generation of an electrical signal to be determined. At the upper limit, the time delay between each pulse must not be so large that the period taken to record the data becomes unreasonably extended. Preferably, the frequency of the pulses is from 2-50 Hz, more preferably 5-15 Hz and most preferably 10 Hz. This corresponds to a time delay between pulses of 20-500 ms, 66-200 ms and 100 ms, respectively. In addition, the so-called "mark-space" ratio, i.e. the ratio of on signal to off signal is preferably one although other ratios may be used to advantage in certain situations. Sources of electromagnetic radiation which produce chopped light with different frequencies of chopping or different mark-space ratios are known in the art. The detector 7 determines the time delay (or "correlation delay") between each pulse of light from light source 6 and the corresponding electrical signal detected by detector 7 from transducer 3. The applicant has found that this time delay is a function of the distance, d.

Any method for determining the time delay between each pulse of light and the corresponding electrical signal which provides reproducible results may be used. Preferably, the time delay is measured from the start of each pulse of light to the point at which a maximum in the electrical signal corresponding to the absorption of heat is detected as by detector 7.

Thus substance 2 may be separated from the transducer surface and a signal may still be detected. Moreover, not only is the signal detectable through an intervening medium capable of transmitting energy to the transducer 3, but different distances, d, may be distinguished (this has been termed "depth profiling") and that the intensity of the signal received is proportional to the concentration of the substance 2 at the particular distance, d, from the surface of the transducer 3.

Figure 2:
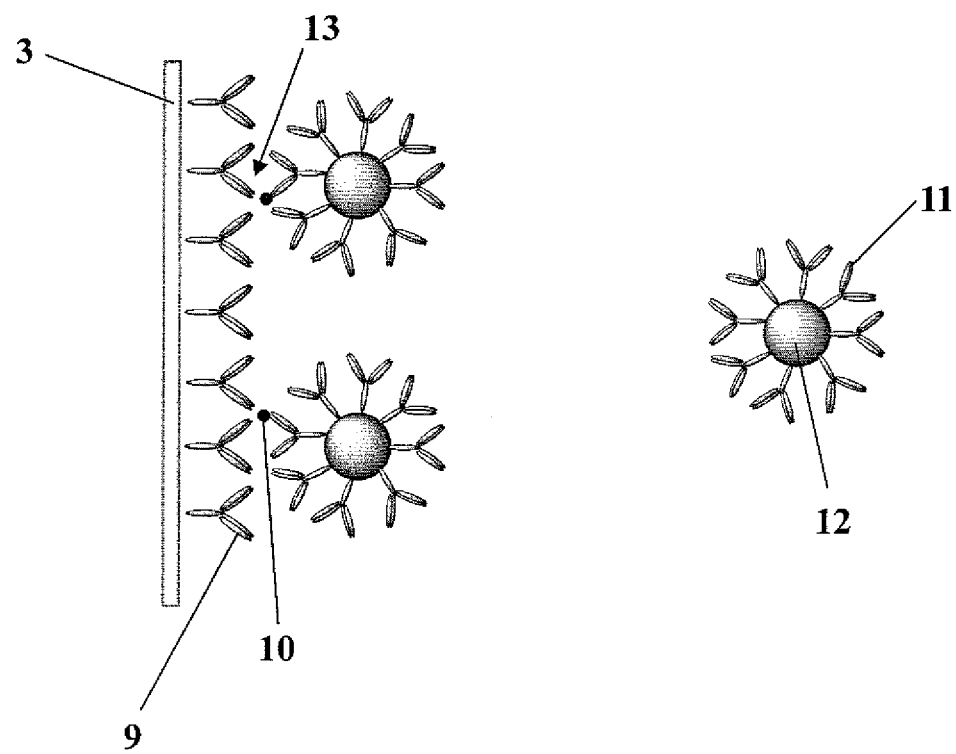
FIG. 2 shows a schematic representation of the method of the present invention.

FIG. 2 shows the incorporation of the device 1 from FIG. 1 in an anti-complex immunoassay of in accordance with the present invention. The transducer 3 is shown in a vertical arrangement, although other orientations are possible and even advantageous in some circumstances. The transducer 3 is coated with a first reagent shown in FIG. 2 as a first antibody 9 (an immobilised capture antibody). The sample also contains an analyte 10 and a second antibody 11 bound to a label 12 (which corresponds to the substance 2 in FIG. 1).

The first reagent 9 has a binding site (a paratope) which is capable of binding the analyte 10 or a derivative of the analyte. The analyte 10 or a derivative of the analyte binds to the first reagent to form a first reagent-analyte complex. A region (epitope) is formed in the first reagent-analyte complex by the binding of the first reagent to the analyte 10 or derivative thereof. The second reagent 11 has a binding site (paratope) which is capable of selectively binding the region thus formed on first reagent-analyte complex and hence when the second reagent 11 is added, it binds to the complex. The binding is selective because the region formed in the first reagent-analyte complex is not present until that first binding event occurs. In a preferred embodiment, the sample and the second reagent are introduced simultaneously.

The first antibody 9 has been raised against the analyte 10 and selectively binds to the analyte 10 when the sample is introduced. By judicious choice of the second antibody 11, reactivity can be chosen against an epitope formed at the junction of the first antibody 9 and the analyte 10, i.e. second reagent 11 has a binding site which is capable of selectively binding the first reagent-analyte complex 13. Thus, the second antibody 11 can only bind to the complex 13 of the first antibody 9 and the analyte 10. No binding of the second antibody 11 can take place in the absence of the analyte 10 and hence the signal obtained from the label 12 attached to the second antibody 11 is directly proportional to the analyte concentration. However, since the second antibody 11 recognises an epitope in the complex, the assay does not require two separate epitopes to be present in the analyte 10, facilitating small molecule detection. Importantly, the method of the present invention permits detection of the binding of the second antibody 11 to the first reagent-analyte complex 13 in real time, without separation and washing steps. This is a significant advantage in the art. Thus, in a preferred embodiment, the assay is carried out without removing the sample from the transducer 3 between the steps of exposing the sample to the transducer 3 and irradiating the sample. Moreover, no further intervention (e.g. to separate bound and unbound second reagent) is required between exposing the transducer to the sample and irradiating the sample.

The second reagent which is not bound to the surface is free to diffuse away from the surface. Preferably the second reagent is allowed to become separated from the surface solely by diffusion.

Although the first and second reagents are exemplified in FIG. 2 by a first and second antibody, the present invention is not limited thereto. Thus, although the first and second reagents are preferably antibodies, other reagents may also be used, such as nucleic acids. In a preferred embodiment, the present invention provides a method of performing an anti-complex antibody immunoassay to detect an analyte (sometimes referred to as a "hapten", being a small molecule which, when attached to a large carrier such as a protein, can elicit an immune response) in a sample, comprising the steps of: providing a transducer having a pyroelectric or piezoelectric element and electrodes which is capable of transducing a change in energy to an electrical signal, a first antibody immobilised on the transducer, the first antibody having a binding site which is capable of binding the analyte or a derivative of the analyte, exposing the sample to the transducer thereby allowing the analyte or a derivative of the analyte to bind to the first antibody to form a first antibody-analyte complex; introducing a second antibody, the second antibody having a binding site which is capable of selectively binding the first antibody-analyte complex, wherein the second antibody has a label attached thereto which is capable of absorbing electromagnetic radiation to generate energy by non-radiative decay; irradiating the sample with electromagnetic radiation; transducing the energy generated into an electrical signal; and detecting the electrical signal. The first antibody is raised to the analyte or derivative thereof, and the second antibody is raised to the complex such that it contains an epitope present in the complex formed between the first antibody and the analyte or derivative thereof, but not present either of the first antibody or analyte/derivative thereof when taken alone.

The first reagent 9 is shown in FIG. 2 attached to the surface of the transducer 3 and is preferably adsorbed on to the transducer. The surface may also be covered by further coatings to stabilise the surface, e.g. Stabilcoat from SurModics Inc, Eden Prairie, Minn., USA.

As discussed with reference to FIG. 2, the second reagent 11 has a label 12 attached thereto. The label 12 is capable of absorbing the electromagnetic radiation generated by the radiation source to generate energy by non-radiative decay. Thus, to detect the presence of the label 12 proximal to the transducer 3, the sample is irradiated with a series of pulses of electromagnetic radiation. The transducer 3 transduces the energy generated into an electrical signal and the electrical signal is detected by detector 7.

The label 12 may be any material which is capable of interacting with the electromagnetic radiation generated by the radiation source to generate energy by non-radiative decay. Preferably the label is selected from, but not limited to, a carbon particle, a coloured-polymer particle (e.g. coloured latex), a dye molecule, an enzyme, a fluorescent molecule, a metal (e.g. gold) particle, a haemoglobin molecule, a magnetic particle, a nanoparticle having a non-conducting core material and at least one metal shell layer, a red blood cell, and combinations thereof.

In the case of a magnetic particle, the electromagnetic radiation is radio frequency radiation. All of the other labels mentioned hereinabove employ light, which can include IR or UV radiation. Preferably the label is a gold particle or a carbon particle. Carbon particles have benefits in that they absorb essentially uniformly at all wavelengths of interest and are much less dense than most metallic particles minimising their sedimentation during the assay. Gold particles are commercially available or may be prepared using known methods (see for example G. Frens, Nature, 241, 20-22 (1973)). For a more detailed explanation of the nanoparticle label see U.S. Pat. No. 6,344,272 and WO 2007/141581. Carbon particles are commercially available, for example, from Degussa, Essen, Germany and methods for their conjugation with proteins and small molecules are known in the art, for example, by Van Doorn et al. (U.S. Pat. No. 5,641,689)

Preferably, the present invention uses a particle having a particle size of 20 to 1,000 nm, more preferably 100 to 500 nm. By particle size is meant the diameter of the particle at its widest point.

The label 12 is proximal to the transducer when the binding event has occurred. That is, the label is sufficiently close to the surface of the transducer for the transducer to be able to detect the energy generated by the label on irradiation of the sample. The actual distance between the label and the surface of the transducer will, however, depend on a number of variables, such as the size and nature of the label, the size and nature of the first and second antibodies and the analyte, the nature of the sample medium, and the nature of the electromagnetic radiation and the corresponding setting of the detector. With regard to the nature of the electromagnetic radiation, the device of the present invention may include a radiation source which is adapted to generate a series of pulses of electromagnetic radiation and the detector is adapted to determine the time delay between each pulse of electromagnetic radiation from the radiation source and the generation of the electric signal thereby allowing a precise determination of the position of the label with respect to the transducer as discussed with reference to FIG. 1.

The unknown sample is expected to contain the analyte, but of course the assay of the present invention may be used to determine the presence or absence of the analyte. The analyte is preferably a small molecule insofar as the assay is ideally suited for such a molecule, although the present invention is not limited thereto. The term "small molecule" used herein is a term of the art and is used to distinguish the molecule from macromolecules such as proteins and nucleic acids. A small molecule is often referred to in the field of immunoassays as a "hapten", being a small molecule which, when attached to a large carrier such as a protein can elicit an immune response and includes molecules such as hormones and synthetic drugs. A small molecule of this type will typically have a molecular weight of 2,000 or less, often 1,000 or less and even 500 or less. The first reagent may be adapted to bind to the analyte itself, although the analyte can undergo a chemical reaction or initial complexing event before binding to the first reagent. For example, the analyte might be protonated/deprotonated in the pH of the assay conditions. Thus, the analyte which is bound to the first reagent may be analyte itself or a derivative of the analyte; both are included within the scope of the present invention.

The sample which may or may not contain the analyte of interest will generally be a fluid sample and usually a biological sample (hence aqueous), such as a bodily fluid, e.g. blood, plasma, saliva, serum or urine. The sample may contain suspended particles and may even be whole blood. An advantage of the method of the present invention is that the assay may be performed on a sample which does contain suspended particles without unduly influencing the results of the assay. The sample will typically be in the order of microliters (e.g. 1-100 µL, preferably 1-10 µL). In order to hold a fluid sample, the transducer is preferably located in a sample chamber and more preferably a well. In a preferred embodiment, the transducer is integral with the chamber, i.e. it forms one of the walls which define the chamber. The sample may simply be retained by surface tension forces, for example, inside a capillary channel.

The present invention also provides a kit for performing the assay described herein. The kit comprises a device for detecting an analyte in a sample substantially as described herein with reference to FIG. 1. The device comprises a transducer having a pyroelectric or piezoelectric element and electrodes which is capable of transducing a change in energy to an electrical signal, a first reagent immobilised on the transducer, the first reagent having a binding site which is capable of binding the analyte or a derivative of the analyte, a source of electromagnetic radiation, and a detector for detecting the electrical signal. The kit further comprises the second reagent. In a preferred embodiment, the second reagent is releasably attached to one of the interior surfaces of the chamber prior to use. By releasably attached is meant that the second reagent is attached to the surface, e.g. by being dried down on to the surface, but is released when the sample is introduced. In a preferred embodiment, the device consists essentially of the above-described features. By "essentially" is meant that no other features are required to perform the assay.

The device may take the form of a hand-held portable reader and a disposable device containing the transducer. The sample is collected in an essentially closed system, mixed with the second reagent and placed in a reader that would perform the irradiation of the sample and detection of the resultant electrical signal.

The present invention further provides for the use of a transducer having a pyroelectric or piezoelectric element and electrodes for detecting a binding event in an anti-complex antibody immunoassay. The anti-complex antibody immunoassay is the assay which involves the binding of the second antibody to the complex of the first antibody and the analyte or derivative of the analyte.

EXAMPLES

Example 1

Preparation of Active Piezo/Pyrofilm Biosensors

A poled piezoelectric polyvinylidene fluoride (PVDF) bimorph film, coated in indium tin oxide used as the sensing device in the following examples, was dip-coated in polystyrene solution (1% in toluene) in a low humidity environment to give a polystyrene layer on top of the indium tin oxide. This was then coated in polystreptavidin solution (200 µg/mL in PBS—10 mmol/L phosphate buffer containing 2.7 mmol/L KCl, 137 mmol/L NaCl and 0.05% Tween) by incubation at room temperature overnight. Polystreptavidin was prepared as described by Tischer et al (U.S. Pat. No. 5,061,640).

To prepare a "capture" surface, the polystreptavidin surface was incubated with biotinylated anti-testosterone (M1), giving an antibody coated surface (C1). 10 ug/mL of biotinylated anti-testosterone (HyTest Ltd, Turku, Finland, Cat #2T2-biotin, or Accurate Chemical Co, Westbury, N.Y., USA, Cat #BHS 113) in PBS was incubated at room temperature overnight and then washed with excess PBS and coated with Stabilcoat (SurModics Inc, Eden Prairie, Minn., USA) before drying at 40° C.

Example 2

Preparation of Secondary Antibodies

Secondary monoclonal antibodies (M2), reactive against the capture antibody (M1)-testosterone complex were raised essentially as described in C. H. Self et al Clin. Chem. 1996, 42, 1527-1531 and biotinylated by methods know to those skilled in the art. For example, a 5 mg/ml antibody solution in PBS (NaCl 150 mmol/L, phosphate 20 mmol/L, pH 7.5) is prepared by dissolving lyophilised antibody, or by dilution. If this solution contains other proteins or Tris or other interfering agents, purify by dialysis or gel filtration. Then prepare an NHS-biotin solution at 20 mmol/L in anhydrous DMSO and add 15 µL of the solution of NHS-biotin to the antibody (1 mL). Incubate for 1 hour at room temperature and then dialyze the antibody against PBS containing sodium azide (0.01%). The biotinylated antibody can be diluted to 1 mg/mL with 0.1% sodium azide and 20% of glycerol for storage at −20° C. or +4° C. The level of biotinylation should be in the range of 1-3 biotins per IgG. This can be estimated by quantitation of biotins or for high biotinylation rates, by a differential quantitation of amines.

Example 3

Preparation of the Reporter Conjugates

Carbon-labelled reporter conjugates were prepared essentially as described by Van Doorn et al. (U.S. Pat. No. 5,641, 689). To prepare antibody coated reporter conjugates (R1), 1 mL of Special Black-4 RCC nominally 150 nm carbon particles (Degussa, Essen, Germany) in 5 mmol/L phosphate buffer, pH 6.2 was incubated with 200 μg/mL polystreptavidin solution overnight at room temperature with shaking, resulting in a streptavidin-coated surface (A1). The resultant carbon conjugate was washed (by centrifugation, pelleting and resuspension). 10 ug/mL of biotinylated secondary monoclonal antibodies (M2), reactive against the capture antibody (M1)-testosterone complex, in PBS was then incubated overnight with 1 mL of this streptavidin-coated carbon particle suspension with shaking. The resultant carbon conjugate (C2) was washed (by centrifugation, pelleting and resuspension) 3 times with 0.05 mol/L borate buffer at pH 8.5 and stored in this buffer in the dark at 4° C.

Example 4

Assay—Antibody-Coated Piezo/Pyrofilm Sensor

Figure 3:
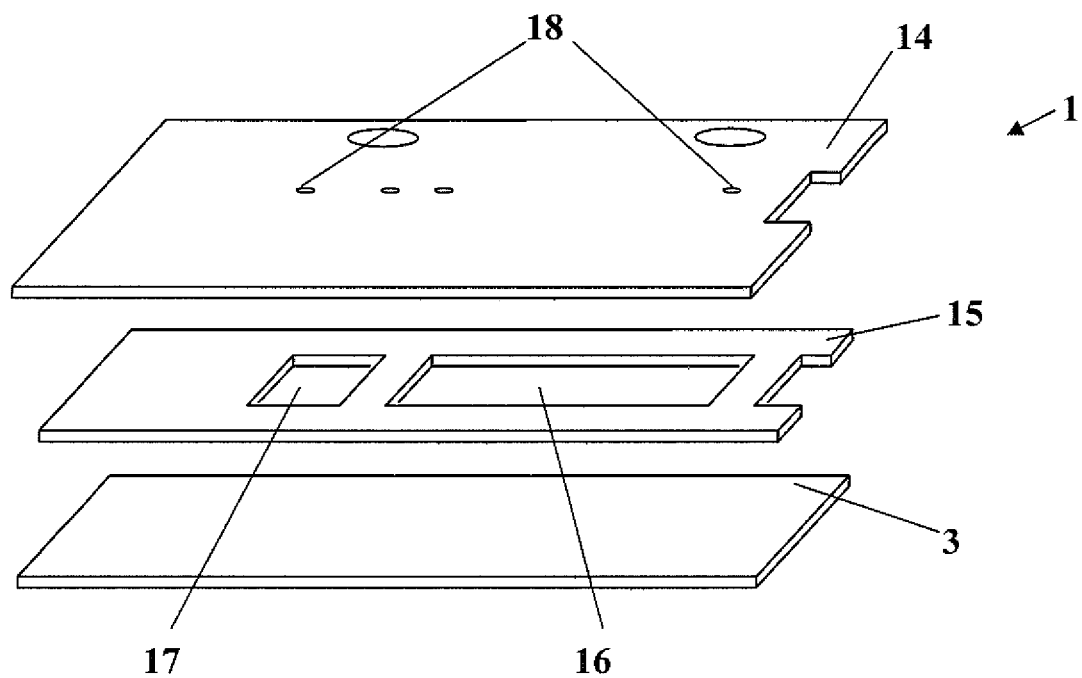
FIG. 3 shows a device according to the present invention.

As shown in FIG. 3, a sensor 1 was fabricated to perform the assay. The sensor 1 is fabricated from a piece of antibody-coated piezofilm 3 (C1, described hereinabove) and a piece of transparent polycarbonate lidding film 14. The films are spaced at a distance of approximately 500 microns using a spacer 15 composed of a piece of pressure sensitive adhesive-coated polyester film die-cut to form two unequally sized chambers 16,17; one chamber 16 of approximate dimensions 30×10×0.5 mm for the assay reaction and a second smaller chamber 17 of dimensions 10×10×0.5 mm for a control reaction. Provision is made to allow for electrical connections to the top and bottom surfaces of the piezofilm in order to detect the charge generated.

Figure 4:
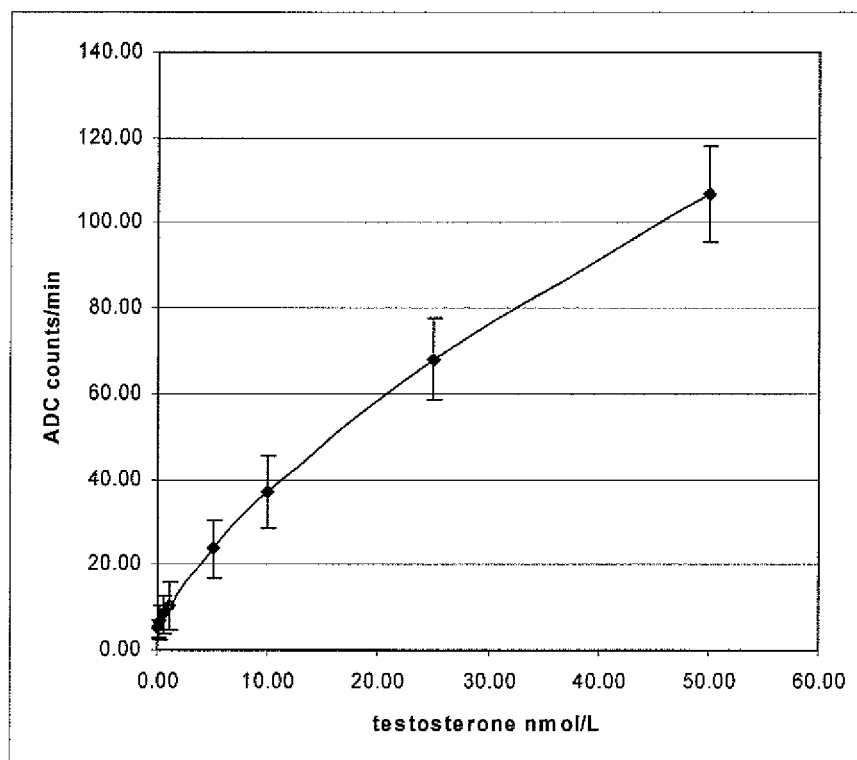
FIG. 4 shows a graph of counts against time, using the method of the present invention.

Assays are carried out by filling the larger chamber 16 (through a fill hole 18) with a mixture of 0.1 mol/L Tris buffer, containing 0.150 mol/L $MgCl_2$ and 0.075% Tween 20 solution, containing 150 nm colloidal carbon particles (at a final concentration of 0.0025% solids) coated with biotinylated antibody (C2, as described hereinabove), reactive against the capture antibody (M1)-testosterone complex, and testosterone standards in PBS to give a final concentration range of 0.1-100 nmol/L. The control chamber 17 is simultaneously filled an identical reaction mix to that in the assay chamber with the testosterone standard replaced with PBS. The entry and exit holes are sealed and the chamber assembly is connected to a test instrument such that the piezofilm 3 is oriented vertically on the side face of the chamber. The piezofilm is then illuminated with chopped LED light sequentially with four LEDs (of wavelength 625 nm), of which three illuminate different areas of the surface of the assay chamber and one illuminates the piezofilm surface of the control chamber. For each LED pulse, a voltage is measured across the piezofilm using a lock-in amplifier and analogue to digital (ADC) converter. The ADC signal is plotted over time and the relationship of ADC counts/min against testosterone concentration is shown in FIG. 4.

The invention claimed is:
1. A method for detecting an analyte in a sample, comprising the steps of:
providing a transducer having a pyroelectric or piezoelectric element and electrodes which is capable of transducing a change in energy to an electrical signal, a first reagent immobilised on the transducer, the first reagent having a binding site which is capable of binding the analyte or a derivative of the analyte,
exposing the sample to the transducer thereby allowing the analyte or a derivative of the analyte to bind to the first reagent to form a first reagent-analyte complex immobilised on the transducer, the binding creating a new reagent-analyte binding region on the first reagent-analyte complex;
introducing a second reagent, which does not bind to the first reagent in isolation and does not bind to the analyte in isolation, wherein the second reagent has a label attached thereto which is capable of absorbing the electromagnetic radiation generated by a radiation source to generate energy by non-radiative decay, the second reagent having a binding site which is capable of selectively binding to the new reagent-analyte binding region created on the first reagent-analyte complex, and thereby immobilising the second reagent and label on the transducer;
irradiating the sample with electromagnetic radiation;
transducing the energy generated by the label into an electrical signal;
detecting the electrical signal; and
using a time delay between the irradiation of the sample and the generation of the electrical signal to determine the presence of label immobilised on the transducer to thereby indicate the presence of analyte in the sample.
2. A method as claimed in claim 1, wherein the first and second reagents are antibodies.
3. A method as claimed in claim 1, wherein the label is selected from a carbon particle, a coloured-polymer particle, a dye molecule, an enzyme, a fluorescent molecule, a metal particle, a haemoglobin molecule, a magnetic particle, a nanoparticle having a non-conducting core material and at least one metal shell layer, a red blood cell, and combinations thereof.
4. A method as claimed in claim 1, wherein the first reagent is adsorbed on to the transducer.
5. A method as claimed in claim 1, wherein the transducer is located in a sample chamber.
6. A method as claimed in claim 5, wherein the chamber is a well.
7. A method as claimed in claim 5, wherein the transducer is integral with the chamber.
8. A method as claimed in claim 1, wherein the sample contains suspended particles.
9. A method as claimed in claim 1, wherein the sample is whole blood.
10. A method as claimed in claim 1, wherein irradiating the sample comprises generating, by the radiation source, a series of pulses of electromagnetic radiation, and detecting the electrical signal comprises detecting, by a detector, only the electrical signal generated by the transducer up to a selected time delay between each pulse of electromagnetic radiation from the radiation source and the generation of the electrical signal.
11. A method as claimed in claim 1, wherein the method is carried out without removing the sample from the transducer between the steps of exposing the sample to the transducer and irradiating the sample.
12. A kit comprising:
(i) a device for detecting an analyte in a sample comprising a transducer having a pyroelectric or piezoelectric element and electrodes which is capable of transducing a change in energy to an electrical signal, a first reagent immobilised on the transducer, the first reagent having a binding site which is capable of binding the analyte or a derivative of the analyte to form a first reagent-analyte complex immobilised on the transducer, the binding creating a new reagent-analyte binding region on the first reagent-analyte complex, a source of electromagnetic radiation, and a detector for detecting the electrical signal; and (ii) a second reagent, which does not bind to the first reagent in isolation and does not bind to the analyte in isolation, wherein the second reagent has a label attached thereto which is capable of absorbing the electromagnetic radiation to generate energy by non-radiative decay, the second reagent having a binding site which is capable of selectively binding to the reagent-analyte binding region created on the first reagent-analyte complex formed between the first reagent and the analyte or the derivative of the analyte and thereby immobilising the second reagent and label on the transducer.

13. A kit as claimed in claim 12, wherein the first and second reagents are antibodies.

14. A kit as claimed in claim 13, wherein the label is selected from a carbon particle, a coloured-polymer particle, a dye molecule, an enzyme, a fluorescent molecule, a gold particle, a haemoglobin molecule, a magnetic particle, a nanoparticle having a non-conducting core material and at least one metal shell layer, a red blood cell, and combinations thereof.

15. A kit as claimed in claim 13, wherein the first reagent is adsorbed on to the transducer.

16. A kit as claimed in claim 13, wherein the device further comprises a sample chamber and the transducer is located in the sample chamber.

17. A kit as claimed in claim 16, wherein the chamber is a well.

18. A kit as claimed in claim 16, wherein the transducer is integral with the chamber.

19. A kit as claimed in claim 13, further comprising a controller configured to control the radiation source to generate a series of pulses of electromagnetic radiation, and wherein the detector is configured to detect only the electrical signal generated by the transducer up to a selected time delay between each pulse of electromagnetic radiation from the radiation source and the generation of the electrical signal.

* * * * *